United States Patent
Gandia et al.

(10) Patent No.: US 12,286,617 B2
(45) Date of Patent: Apr. 29, 2025

(54) METHOD OF PRODUCING FUNGAL MATS AND MATERIALS MADE THEREFROM

(71) Applicant: MOGU S.R.L., Inarzo (IT)

(72) Inventors: Antoni Gandia, Ontinyent (ES); Maurizio Montalti, Amsterdam (NL); Stefano Babbini, Milan (IT)

(73) Assignee: MOGU S.R.L., Inarzo (IT)

( * ) Notice: Subject to any disclaimer, the term of this patent is extended or adjusted under 35 U.S.C. 154(b) by 799 days.

(21) Appl. No.: 17/299,809

(22) PCT Filed: Dec. 5, 2019

(86) PCT No.: PCT/IB2019/060466
§ 371 (c)(1),
(2) Date: Jun. 4, 2021

(87) PCT Pub. No.: WO2020/115690
PCT Pub. Date: Jun. 11, 2020

(65) Prior Publication Data
US 2022/0025318 A1    Jan. 27, 2022

(30) Foreign Application Priority Data
Dec. 6, 2018  (IT) .................. 102018000010869

(51) Int. Cl.
*C12N 1/14*   (2006.01)
(52) U.S. Cl.
CPC ............ *C12N 1/14* (2013.01); *C12N 2513/00* (2013.01)
(58) Field of Classification Search
CPC .............................. C12N 1/14; C12N 2513/00
See application file for complete search history.

(56) References Cited

U.S. PATENT DOCUMENTS

| | | | |
|---|---|---|---|
| 4,021,306 A * | 5/1977 | Soper, Jr. ................. | C12B 1/00 195/81 |
| 5,854,056 A | 12/1998 | Dschida | |
| 8,298,809 B2 | 10/2012 | Kalisz et al. | |

FOREIGN PATENT DOCUMENTS

| | | |
|---|---|---|
| WO | 1999024555 A2 | 5/1999 |
| WO | 2012148995 A1 | 11/2012 |
| WO | 2017151684 A1 | 9/2017 |
| WO | 2018014004 A1 | 1/2018 |

OTHER PUBLICATIONS

Nevo Z. et al., "Novel Injectable Chitosan Mixtures Forming Hydrogels", English translation of AU 2007/331071 A1, published on Jun. 19, 2008 (total 15 pages). (Year: 2008).*
Jiang L et al., Manufacturing of biocomposite sandwich structures using mycelium-bound cores and preforms:, Journal of Manufacturing Processes, vol. 28, Aug. 1, 2017, pp. 50-59.
Notification of Transmittal of the International Preliminary Report on Patentability of PCT/IB2019/060466 of Mar. 23, 2021.
Search Report and Written Opinion of PCT/IB2019/060466 of Jan. 24, 2020.
Sharma A., et al., Reduced toxicity of malachite green decolorized by laccase produced from *Ganoderma* sp. rckk-02 uer solid-state fermentation., 3 Biotech (2015), vol. 5, pp. 621-631.

* cited by examiner

*Primary Examiner* — Satyendra K Singh
(74) *Attorney, Agent, or Firm* — Silvia Salvadori, P.C>; Silvia Salvadori

(57) ABSTRACT

The present invention relates to a method for obtaining a fungal mat comprising the steps of: a) inoculating and growing a filamentous fungal species onto a solid nutritive medium comprising a lignocellulosic material, thereby obtaining a solid nutritive medium colonized by said fungal species; b) mixing said colonized nutritive medium with water or with an aqueous solution and blending at high speed to obtain a homogeneous living fungal slurry; c) pouring the living fungal slurry into a flat container; d) incubating the living fungal slurry until a continuous fungal mat of the desired thickness and density is formed on the top surface of the living fungal slurry; e) harvesting the fungal mat thus obtained; and, optionally f) washing the harvested fungal mat.

13 Claims, 1 Drawing Sheet

METHOD OF PRODUCING FUNGAL MATS AND MATERIALS MADE THEREFROM

This application is a U.S. national stage of PCT/IB2019/060466 filed on 5 Dec. 2019, which claims priority to and the benefit of Italian Application No. 102018000010869 filed on 6 Dec. 2018, the contents of which are incorporated herein by reference in their entireties.

TECHNICAL FIELD

The present application relates to a new method for the production of fungal mats from living fungal slurry and to the products obtained therefrom, in particular for application in soft goods market, as for example leather and textile products.

BACKGROUND ART

The textile industry is one of the most polluting industries in the world and has a substantial impact on the environment.

In recent years, a great deal of attention has been focused on the development of new sustainable and compostable textile materials obtained by the use of environmentally friendly, non-pollutant processes.

In particular, more sustainable processes and materials, based on renewable feedstock, have been proposed in alternative to cotton or petroleum based fibers; examples include pineapple cellulose (Piñatex), grape marc (Vegea), orange fiber and palm-leaf products, to cite a few. Also, in the field of animal derived products, alternatives to the use of animal skin are a growing trend in several markets due to the increase of awareness towards environmental impact and animal welfare. The production of animal leather raises ethical issues and has a negative impact on the environment due to the use of substantial amounts of natural resources as well as of pollutant and toxic chemicals used for the processing of the skins. Different strategies have been proposed in order to produce animal-free and sustainable leather-like materials. For example, products have been obtained from waste materials deriving from apple juice production, pineapple or fungi.

Fungi, in particular, are one of the most abundant and fastest growing living organisms on the planet.

Mycelium is the vegetative structure of the fungi and consist of a network of fine filaments, called hyphae. Hyphae are formed by cells that grow as tubular, elongated structures with a diameter of 2-10 µm and form a tight network of interlocking filaments. The cells are surrounded by the cell wall, which can make up to 30% of the dry weight of the cell and has a composition that mainly consist of β-type glucans, chitin and other structural proteins. Due to the high amounts of chitin in the cell walls and its similarities to cellulose in terms of structure, it has been suggested that fungal pulp could find industrial application as an alternative to wood pulp in the paper, biomedical and textile fields.

Therefore, a number of methods have been developed in the last years for the production of fungal mats in culture for various applications.

These disclosed methodologies for fungal mat production make use of widely known techniques for the propagation of filamentous fungi, such as liquid state fermentation (LSF) and solid state fermentation (SSF).

LSF involves the growth of the microorganisms in a large excess of free water, typically resulting in a microbial suspension in a liquid medium in which various nutrients are dissolved.

On the contrary SSF takes place in a solid growth medium with minimum moisture to support the growth and metabolic activity of microorganisms. Water content in SSF ranges from 30% to 80%, depending on the retention capacity of the substrate material.

U.S. Pat. No. 5,854,056 describes a method, based on LSF, which comprises inoculation of a liquid medium with conidiospores of the fungus and production of mycelia from these spores, followed by the growth of mycelia into flat mats in shallow troughs containing nutritious broth and subsequent recovery of a mycelial mat to be further processed for food, textile and biomedical purposes.

This liquid state fermentation (LSF) method is adapted to fast growing molds as for example *Rhizopus* spp. and *Fusarium* spp., but it cannot be easily applied to basidiomycetes. Normally, fast growing molds growing in LSF don't provide mats with enough density or homogeneity to be suitable as soft materials, being fragile, with low tear and tensile strength and resistance to abrasion, especially after drying. Moreover, when desiccated, the materials described in this patent is extremely brittle.

On the other hand, US2015/003620 and WO2018/0144004 describe methods for the production of fungal materials by solid state fermentation (SSF) and growth of mycelia on the surface of solid nutritive substrates and their subsequent harvesting.

Both methods are based on the harvesting of fungal mats from the surface of flattened solid substrate inoculated with a fungal strain. One of the main differences between the two methods is the use of a porous membrane positioned on top of the solid nutritive substrate colonized by the fungus, as described in WO2018/0144004. The use of such porous membrane apparently eases the separation of the forming mycelial mat from the solid substrate and is also used to direct the growth of the hyphae into a desired spatial pattern and/or geometric orientation.

These last two SSF methods, and in general all SSF based protocols, are very dependent on the distribution and density of the inoculum throughout the solid substrate and very inclined to produce heterogeneous morphologies on surface. The use of randomly distributed solid granular inoculum, usually grain spawn, and the different growth rates on solid substrates, indeed, results inevitably in discontinuities in the forming mat. These result in a lack of homogeneity in the final fungal mat in terms of density, thickness and color and poor mechanical and aesthetic properties, which make them unsuitable to be used in the consumer textile industry.

The general limitations encountered with LSF and SSF, some of them examined above, have also been described in WO2017/151684. To overcome such limitations the inventors of such patent propose a fermentation technique called Solid Substrate Surface Fermentation (SSSF). In this methodology the solid substrate is submerged under the surface of a liquid, such that the fungal mat grows on the surface of the liquid using carbon sources derived from the submerged solid. Nevertheless, this method is still limiting when taking in consideration the poor availability of dissolved oxygen within the static liquid medium. Moreover, the man skilled in the art would understand that even though the method is called SSSF it does not substantially differ from the static liquid surface fermentation described by U.S. Pat. No. 5,854,056 whereas the mat grows on the surface of nutritious liquid.

Also, the processes described to grow these mats, all following standard LSF or SSF techniques, are associated with a high risk of contamination due to the free availability of nutrients for contaminant microbes within the solid substrate or liquid medium. Also, quite frequently, these methods fail to provide good oxygenation to the growing hyphae, limiting this exchange and thus the nutrient trafficking and growth to the surface of the liquid in LSF setups or by suffocating the mycelial matrix on very compacted substrate blocks when following SSF protocols.

Thus, the methods of the prior art allow the production of fungal mats with discontinuous properties especially in terms of aspect, density, thickness and mechanical properties such as tensile and tear strength and resistance to abrasion. In addition, the existing methods require the use of very strict sterile protocols and facilities to secure the operations, which raises the costs of production. Furthermore, as a result of contamination and lack of homogeneous growth of the mats, these methods are characterized by great volume losses and low yields in products suitable to be used for further applications.

It is therefore felt the need for a new method that provides fungal mats with consistent, reproducible and stable properties, in particular that are uniform in both composition and thickness and show improvement of the fungal mat mechanical and aesthetical properties.

Furthermore, it is also felt the need for a method wherein risk of microbial contamination is low and therefore does not require strict sterility conditions to be carried out. It is also a need, to identify a method that allows for a good gas exchange within the grow medium, providing good oxygenation to the growing hyphae. Finally, it is preferable to develop a simple method that does not require porous membranes for easing the harvest of the fungal mat, nor a specific growth pattern or geometric orientation of hyphae.

SUMMARY OF THE INVENTION

The present inventors have found a new method for obtaining fungal mats that allows to solve the above problems encountered with the LSF and SSF methods of the prior art.

In particular, the inventors have found that by blending at high speed a pre-colonized solid nutritive medium comprising high lignocellulose content, with water and/or optional additives in a certain ratio, to obtain a living fungal slurry and incubating the resulting slurry in a flat container, a fine and homogeneous distribution of hyphae and air bubbles within the slurry is always obtained, thereby providing a suitable platform, neither liquid nor solid, but rather gel-like, that allows for the production on its surface of fungal mats having a consistently homogeneous thickness and composition.

Also, by using pre-colonized lignocellulosic material as main nutritive medium during the blending step, the risk of contamination by microorganisms is very low. In fact, the solid nutritive medium, which has been already colonized by the fungus, provides a poor availability of nutrients for contaminant microorganisms, but a large amount of viable hyphae that could be homogeneously chopped and distributed using a high-speed mixer to form the living fungal slurry. Furthermore, the fungus by pre-digesting the growth medium produces and releases its own natural defensive antimicrobial compounds that will be present throughout the homogenized slurry.

Therefore, the method according to the invention provides a living fungal slurry that will supply a high yield of mechanically performing fungal mats suitable for further industrial applications.

Accordingly, a first object of the invention is a method for obtaining a fungal mat comprising the steps of:
a) inoculating and growing a filamentous fungal species onto a solid nutritive medium comprising a lignocellulosic material, thereby obtaining a solid nutritive medium colonized by said fungal species;
b) mixing said colonized nutritive medium with water or with an aqueous solution and blending at high speed to obtain a homogeneous living fungal slurry;
c) pouring the living fungal slurry into a flat container;
d) incubating the living fungal slurry until a continuous fungal mat of the desired thickness and density is formed on the top surface of the living fungal slurry;
e) harvesting the fungal mat thus obtained; and, optionally
f) washing the harvested fungal mat.

A second object of the invention is a mat which is obtained by a method according to the first object of the invention.

Contrary to the mats obtained by the methods of the prior art, the mat obtained by a method according to the first object of the invention is homogeneous in thickness, density, color and has mechanical properties consistent across all its continuous surface.

A third object of the invention is a nonwoven multilayer composite material comprising one or more single layers of fungal mat according to the second object of the invention, alternated with one or more single layers of a porous material.

A fourth object of the invention is a multilayer mat comprising one or more layers of fungal mats and obtained by a method according to the second object of the invention, wherein said mat consists of at least 95% of fungal biomass and said layers comprise fungal hyphae grown without any orderly spatial arrangements or patterns.

A fifth object of the invention is the use of a mat according to the second object of the invention, a multilayer composite material according to the third object of the invention, or a multilayer mat according to the fourth object of the invention, to produce a textile product.

A sixth object of the invention is a textile product comprising a fungal mat according to the second object of the invention, a multilayer composite material according to the third object of the invention, or a multilayer mat according to the fourth object of the invention.

A seventh object of the invention is the use of a mat according to the second object of the invention, a multilayer composite material according to the third object of the invention, or a multilayer mat according to the fourth object of the invention, for the manufacturing of a soft good.

DEFINITIONS

Figure 1:
FIG. 1 shows the harvesting of the fungal mat obtained in Example 1.

The term "soft good" as used herein refers to any product made of, or comprising, a soft flexible material such as textiles and/or leather. These include apparel, cloth, garment, footwear, headwear, sportswear, backpacks and luggage, bedding, linens, consumer electronic accessories, coverings for furniture or automotive etc.

The term "lignocellulosic material" as used herein refers to a material that contains as main components cellulose, hemicellulose and lignin, and, optionally, smaller amounts of pectin, proteins and ash. The relative content of each of these constituents varies depending on the origin of the lignocellulose material.

The term "mat" or "fungal mat", as used herein, refers to a sheet of material formed by interwoven or interconnected fungal hyphae forming a continuous and flat surface. Preferably, said sheet of material exclusively consists of fungal mycelium.

The term "mycelium" as used herein refers to the vegetative body of a filamentous fungus made of a mass of branching filaments, called hyphae.

The term "filamentous fungus" as used herein refers to any member of the group of eukaryotic organisms including ascomycete and basidiomycete fungi that form filamentous structures known as hyphae. Hyphae are multicellular structures that are tubular, elongated and thread-like (filamentous), which may contain more than one nucleus per cell and that grow by branching and extending at their tips.

The term "solid nutritive medium" as used herein refers to a solid substrate that provides both support and nutrients for the growth of fungal mycelia.

The term "pure culture" as used herein refers to an axenic culture in which only one strain or clone is present, in the absence of other organisms or types.

The term "flat container" as used herein is a container comprising a flat base surface enclosed by sides.

The term "porous material" as used herein refers to a material that contains pores, therefore being formed by a skeletal portion (i.e. the "matrix" or "frame") enclosing pores and by fluids (i.e. liquid or gas) filling the pores.

The term "hygienically" as used herein refers to a method that provides a healthy and axenic culture.

The terms "living fungal slurry", "living slurry", "mycelial slurry", "fungal slurry" or eventually just "slurry" as used herein, refer to a viscous fine blend or dispersion of substrate particles, fluids (i.e. liquid or/and gas) and living fungal hyphae.

The terms "blending" or "blending step" as used herein refer to the process of obtaining a living fungal slurry starting from a pre-colonized solid substrate and water by mechanical means suitable to achieve the above-mentioned living fungal slurry.

DETAILED DESCRIPTION OF THE INVENTION

An object of the present invention is a method for obtaining a fungal mat comprising the steps of:
a) inoculating and growing a filamentous fungal species onto a solid nutritive medium comprising a lignocellulosic material, thereby obtaining a solid nutritive medium colonized by said fungal species;
b) mixing said colonized nutritive medium with water or with an aqueous solution and blending at high speed to obtain a homogeneous living fungal slurry;
c) pouring the living fungal slurry into a flat container;
d) incubating the living fungal slurry until a continuous fungal mat of the desired thickness and density is formed on the top surface of the living fungal slurry;
e) harvesting the fungal mat thus obtained; and, optionally
f) washing the harvested fungal mat.

Any species of filamentous fungi may be used in the method of the invention. However, particularly preferred are the fungal species belonging to the basidiomycota divisions. Preferably, said fungal species is selected from *Ganoderma, Trametes, Fomes, Fomitopsis, Phellinus, Perenniporia, Pycnoporus, Tyromyces, Macrohyporia, Bjerkandera, Cerrena* and *Schizophyllum*. The use of other species belonging to the genera *Fusarium, Rhizopus, Aspergillus, Myxotrichum* and *Trichoderma* is also feasible under the method described herein. Particularly preferred species of fungi due to the features of the final mat obtained are *Ganoderma* spp., *Fomes* spp., *Pycnoporus* spp. and *Perenniporia* spp.

According to a preferred embodiment, in step a) a pure culture of a filamentous fungus is inoculated.

Alternatively, a combination of different species or strains of fungi can be used.

Among the above species, strains are preferably selected having advantageous features such as the ability to colonize a substrate in short periods of time, better temperature tolerance, resistance to microbial contamination or specific hyphal branching patterns, mycelium coloration, smell or stiffness.

The selected fungal strains may be mutants or recombinant clones generated within a breeding programme (induced mutagenesis, genetic engineering, etc).

Usually, in step a), inoculating is carried out by adding a liquid or solid inoculum axenically of the fungus onto the solid nutritive medium by using a sterile tool, for example a volumetric pipette or a scalpel.

The liquid inoculum consists in a predetermined volume of a liquid medium containing a sufficient concentration of fungal cells. Preferably, said liquid medium contains an amount of fungal biomass between 5 and 15 g/L and it is added to the solid nutritive medium in a ratio between 5 and 20 ml per Kg of substrate. Liquid media that are suitable to be used for preparation of the inoculum are, for example, Malt Extract Broth (MEB), Malt Yeast Extract Broth (MYEB), Potato Dextrose Broth (PDB), formulations based on the use of liquid molasses in concentrations up to 5% of the volume and side-streams deriving from the processing of lignocellulosic biomass and/or by-products from other industrial processes for example in the agriculture or food industry.

The solid inoculum consists in a solid medium, preferably seeds or sawdust, inoculated with the fungal mycelium deriving from a pure culture in a Petri dish or a liquid culture vial. The selected inoculum is hygienically transferred using a sterile scalpel, forceps or pipette tip under a clean airflow, or poured directly onto the subsequent solid nutritive medium, preferably at ratios from 2 to 5% of inoculum per total weight of solid medium.

The solid nutritive medium is preferably sterilized or pasteurized before inoculation. After inoculation, growth of the fungus is carried out by incubating the inoculated solid nutritive medium in static and aerobic conditions. Preferably, growth of the fungus is carried out in the dark and at a temperature comprised between 20° C. and 30° C., more preferably in the range of 23° C. to 28° C. The growth of the fungus is preferably continued until the exposed area of the solid medium is covered, more preferably completely, by fungal mycelium. Usually, this requires that the growth is carried out for a period comprised between 5 and 15 days, more preferably between 7 and 10 days after inoculation.

According to a preferred embodiment, said solid nutritive medium of step a) consists of at least 90%, preferably 95%, more preferably 98%, even more preferably 100% of its total weight of lignocellulosic material. The lignocellulosic material may also be chemically treated in order to improve its texture, pH and nutritional properties by, for example, adding calcium sulfate, calcium carbonate or other similar mineral amendments or admixed with seeds, seed flour or starch powder.

Accordingly, in an alternative preferred embodiment, said solid nutritive medium comprises as the main component, preferably consists of lignocellulose material admixed with seeds, seeds flour, starch powder, and/or minerals. Preferably, said solid nutritive medium of step a) consists for at least 90%, preferably 95%, more preferably 98%, even more preferably 100% of its total weight of lignocellulosic material admixed with seeds, seed flour, starch powder, and/or minerals.

Preferably, said seeds are whole seeds selected from millet, rye, sorghum, rice, wheat, corn whole seeds. Preferably said seed flour is obtained from millet, rye, sorghum, wheat, rice, corn whole seeds. Preferably, said minerals are selected from calcium sulfate and calcium carbonate.

Preferably, the lignocellulosic material for use in the method of the invention is selected from agroindustry lignocellulosic biomass, consisting for example of agricultural crop residues, energy or purpose crops, non-agricultural by products from forestry, paper industry, food and biofuel production, or a combination thereof. The solid nutritive medium is selected according to metabolic needs of the specific fungus used. For example, basidiomycete species belonging to the order polyporales will require a higher content of lignocellulosic materials such as found in wood and straw, while other fungi belonging to other divisions, could require the presence of a percentage of readily available carbohydrates, such as those found in wheat bran and flour.

The skilled man would know on the basis of common general knowledge and bibliographical references which lignocellulosic material to select for each fungal species used.

In step b), said colonized solid nutritive medium is mixed with water or an aqueous solution, preferably sterile or sanitized, and then blended to obtain a homogeneous, viscous and living fungal slurry with physical properties that are in between those of a liquid and a solid, resulting similar to a gel state. Preferably, the colonized medium and water or aqueous solution are mixed in a ratio of between 0.5 and 3 g, more preferably 2 g, of colonized medium per 10 ml of water.

The mixture is blended in a high speed mechanical blender, suitable to the amount of material processed, for at least 30 seconds, preferably at least three minutes, and more preferably at least five minutes, until obtaining a living fungal slurry.

According to a preferred embodiment, the mixture is blended in a high speed mechanical blender at a speed of at least 10,000 rpm, preferably at least 15,000 rpm, and more preferably at least 20,000 rpm. Preferably, the mixture is blended in a high speed mechanical blender at a speed of no more than 80,000 rpm, preferably no more than 70,000 rpm, and more preferably no more than 60,000 rpm. In a particular embodiment, the mixture is blended in a high speed mechanical blender at a speed of from 30,000 to 50,000 rpm.

Preferably, the living fungal slurry obtained in step b) has a viscosity of from 1,000 to 40,000 cps, preferably from 4,000 to 30,000 cps, and more preferably of from 10,000 to 20,000 cps.

Preferably, water is non-treated regular tap water, sterile water, distilled water, or any of these with the addition of water peroxide ($H_2O_2$) in a concentration ranging between 0.009 and 0.05% of the total volume.

The above aqueous solution can derive entirely or partially from the recycled effluent separated from the mat in harvesting step e), which has been treated with $H_2O_2$ to reduce the microbial count.

The addition of foaming agents to the water will result in a foamy substance rich in air bubbles which normally benefit the growth of the fungal mycelium. Such foaming agents are preferably of natural origin such as carrageenan (0.1-1%) or albumin (0.1-1%), but not limited to these.

In step c), the living fungal slurry is poured into a flat container of the desired form and size. Preferably, the living fungal slurry is added in an amount that completely covers the inner flat base surface of the container. Preferably, the layer of living fungal slurry covering the inner flat base surface of the container has a thickness of from 0.2 to 5 cm, preferably from 0.5 to 1.5 cm to avoid compaction and thus the anaerobic suffocation of the hyphae.

Additives such extra nutrients, preferably carbohydrates, more preferably sucrose, dextrose, malt extract or molasses, and/or foaming agents, culture hygienization agents such as $H_2O_2$ or pH regulators may be optionally added to the slurry, before or after pouring into the container, depending on the specific fungus and operative conditions used.

The pH regulators are preferably selected from sorbic acid, acetic acid, benzoic acid, propionic acid acids and their sodium salts.

For example, culture hygienization agents such as water peroxide are added when working in non-sterile conditions, for example when the living fungal slurry is prepared using tap water or in a non-sterile environment.

According to an embodiment, one layer of porous material can also be added on the surface of the living fungal slurry once this has been poured into the flat container, thus forming in step d) a multilayer composite mat comprising one layer of fungal mycelium and one layer of porous material. According to an alternative of this embodiment, a number of alternate layers of slurry and porous material may be added into the container in step c), thereby originating in step d) a multilayer composite mat.

Preferably, the porous material is selected from the group consisting of fibrous materials or polymers. The term "fibrous material" as used herein refers to a material that contains natural fibers, such as for example, but not limited to, hemp, cotton or linen. The term "polymer" as used hereby refers to a polymer that can be used as reinforcement fusion fiber or binder for the fungal mats. Such polymers may be comprised of a synthetic polymer or much more preferably a natural and/or biodegradable polymer, such as for example, but not limited to, polyhydroxyalkanoates (PHA), polyglycolic acid (PGA), poly-ε-caprolactone (PCL), polycaprolactone (PCL), polylactic acid (PLA), cellulose acetate, chitin/chitosan, corn zein and/or starch.

Preferably, said porous material is a fabric. According to one preferred embodiment, said fabric has a natural origin, more preferably it is selected from hemp, cotton or linen. According to one alternative preferred embodiment, said fabric is made of a synthetic polymer or a blend of a natural and a synthetic polymer. According to a particularly preferred embodiment said fabric is biodegradable.

In case non-biodegradable synthetic polymers are utilized, the material should be suitable to allow effective separation between the fungal layer and the synthetic polymer layer at the end of life of the product.

The incubation step d) is carried out maintaining the container horizontally, in static and aerobic conditions at constant temperature. Preferably, the container is covered with a lid featuring a system that allows a controlled gas exchange between the inner volume of the container and the external environment. Depending on the fungal species and the desired growing conditions, a constant $CO_2$ concentration, preferably between 2000-2500 ppm, is maintained by monitoring the $CO_2$ concentration in the incubation enclosures by means of electronic sensors. Incubation is carried out until a continuous mycelial mat of the desired density and thickness is formed on top of the slurry. Preferably, this requires that incubation is carried out for a period between 8 and 20 days, more preferably between 10 and 18 days, even more preferably of 15 days. Longer incubation times produce, in general, thicker and more resistant mats.

Once the mat has reached the desired thickness and density, it is harvested as shown in FIG. 1. Advantageously, the desired thickness is ranging from 0.1 to 6.0 mm, preferably from 0.2 to 5.0 mm, and more preferably from 0.3 to 4.0 mm. Particularly, the desired density is ranging from 0.1 to 2.0 $g/cm^3$, preferably from 0.3 to 1.7 $g/cm^3$, and more preferably from 0.5 to 1.4 $g/cm^3$.

Preferably, the fungal mat of step e) is harvested by separating it from the digested effluents laying underneath. More preferably, harvesting is carried out by peeling the fungal mat out of the container leaving behind the effluents or undigested fraction of the slurry.

As previously described, the effluent from the harvesting step can be treated and recycled in the process as aqueous solution for the preparation of the slurry in step b).

After harvesting, the method preferably comprises a further step f), after step e), wherein said harvested fungal mat is washed, preferably by rinsing its surface or soaking it with/in water, in order to eliminate any effluent or debris.

Depending on the properties of the final product that one desires to obtain, the method of the invention may further comprise a step g), preferably after washing step f), wherein the fungal mat is chemically and/or physically treated, to improve properties such as appearance, wettability or hydrophobicity, chemical resistance, wear resistance, hardness, antimicrobial activity, active compounds release.

Preferably, in step g), the mat is treated with a plasticizer and/or a crosslinker.

Preferably, said plasticizer is glycerol, more preferably a glycerol solution with a concentration between 10 and 20% (v/v).

Preferably, said crosslinker is one of the chemical reagents already usually employed for leather tanning, preferably genipin.

After step g), the mat can be subjected to a further washing step, step f'), in order to remove any residue or debris from the growth medium.

After step f), and/or g) and/or f') if present, the mat is preferably subjected to a further step, step h), wherein it is dried. Drying is preferably carried out in a chamber with controlled and stable conditions, as granted for instance by a heated vacuum machine. The drying step may be carried out according to the standards existing in the traditional leather manufacturing processes.

When the drying step reaches temperatures above 70° C., it also contributes to stop the biological activity of the fungus.

According to one embodiment, the fungal mat obtained in step h) may be subjected to one or more further finishing steps i) wherein the mat is treated or further treated with plasticizers or crosslinkers, as defined above, to improve its mechanical and aesthetic properties including but not limited to flexibility, texture and colour. After said finishing step, the mat is preferably further washed and dried.

Furthermore, the above described method may also comprise a further step, l), after step e) or f) and before step g), wherein two or more fungal mats are placed one on top of the other, and incubated, preferably at the same incubation conditions previously described for step d) for a period of time of at least two days, preferably from 2 to 7 days, thereby obtaining multilayer mats.

After harvesting and washing, the mats are still in living state and, during incubation, new hyphae will grow from both the juxtaposed surfaces of the mats forming a natural bond between the two mats. This step can be repeated several times by adding new mats as additional layers. The resulting material will be a thicker mat, composed by several layers, with enhanced mechanical properties, specifically with increased tear, flexural and tensile strength. The method described does not induce any changes in the growth pattern of the hyphae and does not require any additional material.

A second object of the invention is a mat obtained by a method according to the first object of the invention.

The mat obtained by the method according to the invention shows homogeneity in thickness, density, color and general mechanical properties, in particular tensile and tear strength and resistance to abrasion, across the mat that is not obtained with the methods of the prior art.

Preferably, the fungal mat is composed of a fungal species belonging to the basidiomycota divisions. Preferably, said fungal species is selected from *Ganoderma, Trametes, Fomes, Fomitopsis, Phellinus, Perenniporia, Pycnoporus, Tyromyces, Macrohyporia, Bjerkandera, Cerrena* and *Schizophyllum*. Different species produce mats of different colours and textures; for example *Fomes fomentarius* produces a brownish and velvety mat with a pleasant smell, *Pycnoporus cinnabarinus* and *Ganoderma lucidum* procure a yellowish or sometimes orange-like, gritty surface.

Accordingly, an object of the invention is a fungal mat composed of a fungus selected from *Fomes fomentarius, Pycnoporus cinnabarinus* and *Ganoderma lucidum*.

The method according to the first object of the invention allows to obtain mats that have properties similar to those of leather. In particular, when the fungal mat is harvested it can already be considered a nonwoven leather-like material, whose technical properties can be further enhanced by means of plasticizers and crosslinkers.

As described above, the method according to the invention allows to obtain multilayer and composite nonwoven materials.

When alternate layers of slurry and porous materials are added to the container of step c), as described above, a composite mat is obtained.

Accordingly, a third object of the invention is a multilayer composite material comprising one or more layers of fungal mats according to the second object of the invention alternated with one or more layers of a porous material, preferably a polymer or fibrous material, as defined above. The multilayer composite material is obtained by the method of the invention as described above.

When the mats obtained by step e) and f) are further processed according to step l), a multilayer fungal mat is obtained.

A fourth object of the invention is a multilayer mat comprising two or more layers of fungal mycelium, wherein said mat consists of at least 95%, preferably 98%, more preferably 100% of fungal biomass and comprises fungal hyphae grown without any spatial arrangements. The hyphae do not show any specific geometric pattern or preferential direction or disposition. The multilayer mat is obtained by the method of the invention, as described above.

The fungal mats of the invention may find application in different fields such as soft goods including textiles, leather, apparel, footwear, automotive, membrane, consumer electronics, accessories and bandaging etc.

A fifth object of the invention is the use of a mat obtained according to the first object of the invention, a multilayer composite material according to the third object of the invention, or a multilayer mat according to the fourth object of the invention for the manufacturing of a textile product.

A sixth object of the invention is a textile product comprising a fungal mat second object of the invention, a multilayer composite material according to the third object of the invention, or a multilayer mat according to the fourth object of the invention.

A seventh object of the invention is the use of a mat according to the second object of the invention, a multilayer composite material according to the third object of the invention, or a multilayer mat according to the fourth object of the invention, for the manufacturing of a soft good product, preferably a textile product.

EXAMPLES

Example 1

A pure culture of the fungus *Ganoderma lucidum* preserved in a Potato Dextrose Agar (PDA) slant tube was plated on several Malt Extract Agar (MEA) Petri dishes and these were incubated for 5 days at 28° C. to create a working stock that could be preserved for at least one week under refrigeration.

Healthy, vigorous and homogeneous sectors of mycelia growing on the Petri dishes were selected and, under clean airflow, transferred using a sterile scalpel to several liquid culture flasks containing Malt Yeast Extract Broth (MYEB), being incubated for 3 days in a shaking incubator at 28° C. and 200 rpm. These liquid cultures were then used to inoculate pasteurized (72 C for 1.5 h) 3.2 kg solid substrate bags containing a 50/50 mixture of hemp shavings (800 g) and soy husks (800 g) with a moisture content of 50% (1600 mL H2O). After 7 days of incubation at room temperature (circa 23° C.) the colonized substrates were manually separated in little chunks and mixed with water, in a proportion of 600 g of colonized substrate per 3000 ml of water, and blended at 45,000 rpm by mechanical means by using a 4 L sterile laboratory blender (autoclaved at 121° C. for 30 min.) to obtain a living slurry containing mycelia and growth medium elements. The mycelial slurry was poured flat into flat containers of 55×55 cm and then incubated in static conditions at room temperature for two weeks to form a homogeneous and continuous fungal mat on the surface that was manually harvested from the spent effluent laying below.

The fungal mat obtained was moved apart from the spent slurry effluent as seen in FIG. 1, manually washed with tap cold water and dried by using a heated vacuum table.

Example 2

A preselected culture of *Fomes fomentarius* preserved at −80 C in 10% glycerol cryovials was plated on several Potato Dextrose Agar (PDA) Petri dishes that were subsequently incubated for 5 days at 28° C. to create a short-term working stock. Vigorous sectors of mycelia growing on the Petri dishes were selected and transferred to polypropylene (PP5) filtered bags containing sterilized barley grains amended with 2% CaSO4 and at a total moisture content of 55%. After 7 days of incubation at room temperature (circa 23° C.) the colonized grains were blended with water, in a proportion of 200 g of colonized substrate per 1000 ml of water, and blended at 45,000 rpm by mechanical means to obtain a living slurry containing mycelia and growth medium elements. Said fungal slurry was poured flat into flat containers and then incubated in static conditions for two weeks to form a fungal mat comprised of pure mycelium that was manually separated from the spent slurry, also referred herein as effluent. The fungal mat was then washed and soaked with a 10% glycerol solution, finally dried by using a heated vacuum curing table.

The product obtained resembles animal leather in touch, color and general mechanical properties.

Example 3

An axenic and preselected culture of *Schizophyllum commune* was grown in several Petri dishes containing Malt Extract Agar (MEA) in order to create a working stock and to discard senescent, contaminated or amorphous phenotypes. Vigorous mycelial sectors from those Petri dishes, showing fast growth and outstanding mycelial density, were cut from the agar and transferred with a flamed scalpel to a sterile laboratory blender containing a certain amount of sterile water. The selected mycelial sectors were then blended at max speed for one minute and used to inoculate substrate bags containing sterilized 50/50 mixture of *miscanthus* chopped (800 g) straw and soy husks (800 g) at a 50% moisture content (total weight of each individual bag was 3.2 kg). Said inoculated substrate bags were then incubated for three weeks at room temperature (circa 23 C) and blended with water in a proportion of 200 g per Liter of water to form a living fungal slurry by using a high-speed sterile laboratory blender as in Example 1. The fungal slurry was then transferred to 35×35 cm flat containers in form of trays inside an incubator chamber under controlled parameters of light (dark), humidity (>80%), ventilation (constant 2000 ppm CO2 levels) and temperature (25 C). Said fungal slurry was incubated flat and static for three weeks, when the forming fungal mat growing on the surface of the fungal slurry achieved the desired thickness and density values. The fungal mat was then harvested by peeling it off the enclosure and washing it to clean its surface from any possible coarse effluent lying beneath. The washed fungal mat was soaked in plasticising solution of 10% glycerol overnight, finally it was wrung and dried by using heated vacuum curing table.

Figure 2:
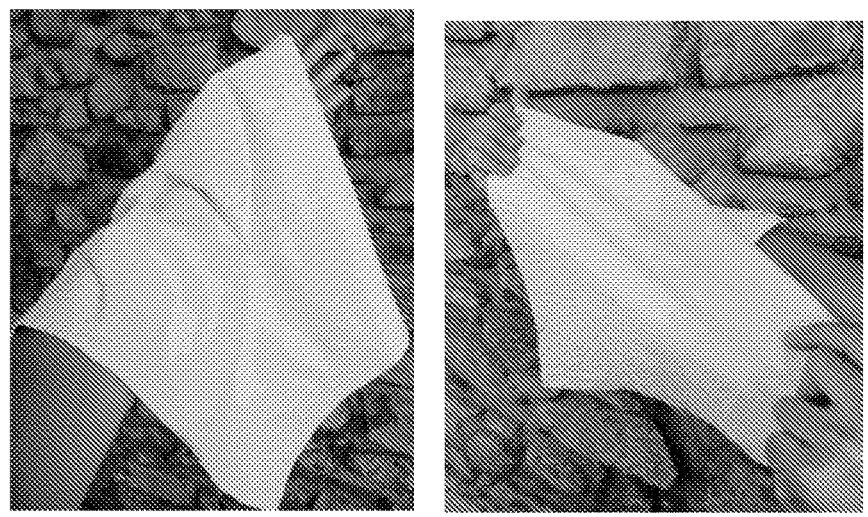
FIG. 2 shows a piece of the fungal mat obtained in Example 3.
Figure 3:
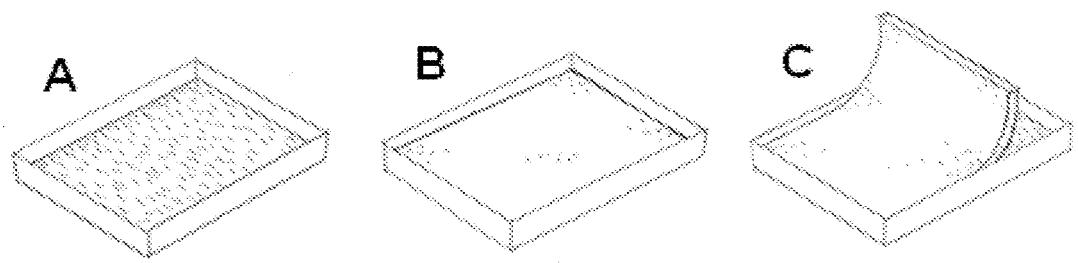
FIG. 3 shows a schematic production process in three basic steps, namely step A wherein a living fungal slurry is poured into a flat container, step B wherein a fungal mat grows on top of the slurry during incubation, and step C wherein the mat is harvested leaving the digested effluent into the flat container.

The product obtained, as seen in FIG. 2, was a continuous and homogeneous leathery mat, with consistent thickness of 2 mm and outstanding flexibility, with formal qualities (e.g. form/size) replicating the ones of the enclosure.

Example 4

As described in examples 1-3, wherein the finished fungal mat is combined with other fungal mats of the same typology/origin in a multilayer fashion to increase the thickness and mechanical resistance of the final piece. The mats are combined one on top of the other while still alive, right after harvesting, and then re-incubated under the same previous conditions for 48 h to allow their hyphae to fuse together, resulting in the adhesion of the mats to form a single continuous piece. The product obtained has an increased thickness and enhanced mechanical properties such as higher tensile and flexural strength, tear resistance, puncture resistance and better heat insulation than the individual mats from which it originates.

The invention claimed is:

1. Method for obtaining a fungal mat comprising the steps of:
   a) inoculating and growing a filamentous fungal species onto a solid nutritive medium comprising a lignocellulosic material, thereby obtaining a solid nutritive medium colonized by said fungal species;
   b) mixing said colonized solid nutritive medium with water or with an aqueous solution and blending at a speed of at least 10,000 rpm to obtain a homogeneous living fungal slurry;
   c) pouring the living fungal slurry into a flat container;
   d) incubating the living fungal slurry until a continuous fungal mat of the desired thickness and density is formed directly on the top surface of the living fungal slurry without any spatial manipulation;
   e) harvesting the fungal mat thus obtained; and, optionally
   f) washing the harvested fungal mat.

2. Method as claimed in claim 1, wherein said fungal species is selected from species belonging to the basidiomycota division.

3. Method as claimed in claim 1, wherein said solid nutritive medium consists of at least 90% of its total weight of lignocellulosic material or of a lignocellulosic material admixed with seeds, seed flour, starch powder, and/or minerals.

4. Method as claimed in claim 1, wherein in step c), a layer of porous material is added on the surface of the fungal slurry once this has been poured into the flat container and, optionally, further alternate layers of slurry and porous material are added, thereby originating in step d) a multilayer composite material comprising one or more layers of fungal mycelium alternated with one or more layers of porous material.

5. Method as claimed in claim 4 wherein said porous material is selected from the group consisting of fibrous materials and polymers.

6. Method as claimed in claim 5 wherein said fibrous material is selected from the group consisting of hemp, cotton and linen.

7. Method as claimed in claim 5 wherein said polymer is selected from the group consisting of polyhydroxyalkanoates (PHA), polyglycolic acid (PGA), poly-ε-caprolactone (PCL), polycaprolactone (PCL), polylactic acid (PLA), cellulose acetate, chitin, chitosan, corn zein and starch.

8. Method as claimed in claim 1, further comprising step g), treating the fungal mat with a plasticizer and/or a crosslinker to obtain a treated fungal mat.

9. Method as claimed in claim 8, further comprising step h) drying said treated fungal mat, after step f) or g).

10. Method as claimed in claim 8, further comprising a step, l) placing two or more fungal mats one on top of the other and incubating for a period of time of at least two days thereby obtaining a multilayer mat having two or more layers of fungal mycelium, after step e) or f) and before step g).

11. The method as claimed in claim 2, wherein said fungal species is selected from the group consisting of *Ganoderma, Trametes, Fomes, Fomitopsis, Phellinus, Perenniporia, Pycnoporus, Tyromyces, Macrohyporia, Bjerkandera, Cerrena* and *Schizophyllum*.

12. The method as claimed in claim 8, wherein said plasticizer is glycerol and said crosslinker is genipin.

13. The method as claimed in claim 10, wherein the two or more fungal mats are incubated from 2 to 7 days.

* * * * *